United States Patent
Zhu et al.

(10) Patent No.: US 11,726,157 B2
(45) Date of Patent: Aug. 15, 2023

(54) DENOISING MAGNETIC RESONANCE FINGERPRINTING USING GENERAL NOISE MODELS

(71) Applicant: THE REGENTS OF THE UNIVERSITY OF MICHIGAN, Ann Arbor, MI (US)

(72) Inventors: Matthew Zhu, Ann Arbor, MI (US); Yun Jiang, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 17/526,549

(22) Filed: Nov. 15, 2021

(65) Prior Publication Data

US 2023/0152405 A1 May 18, 2023

(51) Int. Cl.
  *G01R 33/56* (2006.01)
  *A61B 5/055* (2006.01)
  *G06T 7/00* (2017.01)
  *G06T 5/00* (2006.01)

(52) U.S. Cl.
  CPC ......... *G01R 33/5608* (2013.01); *A61B 5/055* (2013.01); *G06T 5/002* (2013.01); *G06T 7/0012* (2013.01); *G06T 2207/10088* (2013.01)

(58) Field of Classification Search
  CPC ..... G01R 33/5608; A61B 5/055; G06T 5/002; G06T 5/0012; G06T 5/10088
  See application file for complete search history.

(56) References Cited

U.S. PATENT DOCUMENTS

| 7,429,860 B2 * | 9/2008 | Taylor | G01R 33/4625 324/307 |
| 2006/0293587 A1 * | 12/2006 | Taicher | A61B 5/4872 600/410 |
| 2008/0039708 A1 * | 2/2008 | Taicher | A61B 5/055 600/410 |
| 2009/0263001 A1 * | 10/2009 | Ding | G06T 5/007 382/131 |

(Continued)

OTHER PUBLICATIONS

Jiang et al., "MR Fingerprinting Using Fast Imaging With Steady State Precession (FISP) With Spiral Readout", Magn Reson Med. 74(6), Dec. 2015, pp. 1621-1631.

(Continued)

*Primary Examiner* — Dixomara Vargas
(74) *Attorney, Agent, or Firm* — Marshall, Gerstein & Borun LLP

(57) ABSTRACT

A method for denoising magnetic resonance images and data is disclosed herein. An example method includes receiving a series of MRF images from a scanning device; identifying one or more subsets of voxels for the series of MRF images; generating one or more sets of eigenvectors, each set of the one or more sets of eigenvectors corresponding to one of the one or more subsets of voxels, and each eigenvector of the one or more sets of eigenvectors having a corresponding eigenvalue; applying a noise distribution model to each of the eigenvalues; identifying a subset of the eigenvalues as corresponding to noise based on the noise distribution model; and reconstructing the series of MRF images without the subset of eigenvalues identified as corresponding to noise.

26 Claims, 7 Drawing Sheets
(3 of 7 Drawing Sheet(s) Filed in Color)

(56) References Cited

U.S. PATENT DOCUMENTS

| | | | |
|---|---|---|---|
| 2010/0289494 A1* | 11/2010 | Wald | G01R 33/3415 |
| | | | 324/318 |
| 2013/0266239 A1* | 10/2013 | Ding | G06T 5/002 |
| | | | 382/260 |
| 2014/0212015 A1* | 7/2014 | Ding | G06T 5/50 |
| | | | 382/131 |
| 2016/0247263 A1* | 8/2016 | Mailhe | G06T 5/10 |
| 2018/0120404 A1* | 5/2018 | Novikov | A61B 5/055 |
| 2019/0265322 A1* | 8/2019 | Griswold | G01R 33/5608 |
| 2020/0341102 A1* | 10/2020 | Eck | G01R 33/4828 |
| 2021/0076972 A1* | 3/2021 | Novikov | A61B 5/0042 |

OTHER PUBLICATIONS

Marcenko et al., "Distribution of Eigenvalues for Some Sets of Random Matrices", Math. USSR—Sbornik, Vo. 1, No. 4, 1967, pp. 457-483.

Ma et al., "Magnetic Resonance Fingerprinting", Nature, 495(7440), Mar. 14, 2013, pp. 187-192.

Veraart et al., "Denoising of Diffusion MRI Using Random Matrix Theory", Neuroimage, 142, Nov. 15, 2016, pp. 394-406.

Cordero-Grande et al., "Complex Diffusion-Weighted Image Estimation Via Matrix Recovery Under General Noise Models", Neuroimage, 200, Oct. 15, 2019, pp. 391-404.

Robson et al., "Comprehensive Quantification of Signal-to-Noise Ratio and g-Factor for Image-Based and k-Space-Based Parallel Imaging Reconstructions", Magn Reson Med, 60(4), Oct. 2008, pp. 895-907.

\* cited by examiner

DENOISING MAGNETIC RESONANCE FINGERPRINTING USING GENERAL NOISE MODELS

FIELD OF THE DISCLOSURE

The present disclosure generally relates to noise estimate and reduction and, more particularly, to denoising before reconstructing and/or mapping image data.

BACKGROUND

When sampling image data for tissues, some amount of noise is measured from the system performing the measurement. Accurately estimating and removing noise improves the estimation of tissue properties and map quality in the imaging process. Present techniques for such denoising rely empirically setting thresholds or predicting noise before setting a threshold using already-measured data. In other words, present techniques rely on modelling the actual signal and, as such, are parameter-specific and/or imprecise. As such, an accurate and generalized method for denoising is desired.

SUMMARY

In an embodiment, the present invention is a method for denoising magnetic resonance fingerprinting (MRF) acquisitions. The method includes: receiving, by one or more processors, a series of MRF images from a scanning device; identifying, by the one or more processors, one or more subsets of voxels for the series of MRF images; generating, by the one or more processors, one or more sets of eigenvectors, each set of the one or more sets of eigenvectors corresponding to one of the one or more subsets of voxels, and each eigenvector of the one or more sets of eigenvectors having a corresponding eigenvalue; applying, by the one or more processors, a noise distribution model to each of the eigenvalues; identifying, by the one or more processors, a subset of the eigenvalues as corresponding to noise based on the noise distribution model; and reconstructing, by the one or more processors, the series of MRF images without the subset of eigenvalues identified as corresponding to noise.

In a variation of this embodiment, the noise distribution model is a general noise model.

In another variation of this embodiment, the general noise model follows a Marcenko-Pastur distribution.

In yet another variation of this embodiment, identifying the subset of the eigenvalues as corresponding to noise includes: selecting a first subset of the eigenvalues as corresponding to noise; calculating an average of the first subset of the eigenvalues; comparing the average of the first subset of eigenvalues to a corresponding average predicted by the general noise model; and identifying, based on the comparison, the first subset of the eigenvalues as corresponding to noise.

In still yet another variation of this embodiment, the average of the first subset of the eigenvalues is greater than the corresponding average predicted by the general noise model, and identifying the subset of the eigenvalues as corresponding to noise further includes iteratively performing, until a new average of the first subset of the eigenvalues is less than or equal to the new corresponding average predicted by the general noise model, each of: removing at least one eigenvalue from the first subset of the eigenvalues; calculating a new average of the first subset of the eigenvalues; and comparing the new average of the first subset of the eigenvalues to a new corresponding average predicted by the general noise model.

In another variation of this embodiment, a set of signal eigenvalues includes the eigenvalues without the subset of eigenvalues identified as corresponding to noise, and the method further comprises: applying a pre-calculated signal model to the set of signal eigenvalues after identifying the subset of eigenvalues as corresponding to noise.

In yet another variation of this embodiment, the method further comprises performing, prior to identifying the one or more subsets of voxels, a noise decorrelation procedure for the scanner.

In still yet another variation of this embodiment, the noise decorrelation procedure is to decorrelate signals from one or more coils of the scanner.

In another variation of this embodiment, the method further comprises comparing the reconstructed series of MRF images to a pre-calculated dictionary; and constructing, based on the comparison, at least a T1 map and a T2 map of the series of MRF images.

In yet another variation of this embodiment, the eigenvalues are complex values.

In still yet another variation of this embodiment, generating the one or more sets of eigenvectors includes performing singular vector decomposition on the one or more subsets of voxels.

In another variation of this embodiment, the singular vector decomposition is compressed singular vector decomposition.

In yet another variation of this embodiment, the patches of voxels are no larger than 3 by 3 voxel patches.

In still yet another variation of this embodiment, the method is performed agnostic to the type of body tissue being scanned.

In another embodiment, the present invention is a system for denoising magnetic resonance fingerprinting (MRF) acquisitions. The system includes a scanning device configured to perform MRF operations and transmit a series of MRF images; and one or more processors and computer-readable media storing machine readable instructions that, when executed, cause the system to: receive the series of MRF images from the scanning device; identify one or more subsets of voxels for the series of MRF images; generate one or more sets of eigenvectors, each set of the one or more sets of eigenvectors corresponding to one of the one or more subsets of voxels and each eigenvector of the one or more sets of eigenvectors having a corresponding eigenvalue; apply a noise distribution model to each of the eigenvalues; identify a subset of the eigenvalues as corresponding to noise based on the noise distribution model; and reconstruct the series of MRF images without the subset of eigenvalues identified as corresponding to noise.

In a variation of this embodiment, the noise distribution model is a general noise model.

In another variation of this embodiment, the general noise model follows a Marcenko-Pastur distribution.

In yet another variation of this embodiment, identifying the subset of the eigenvalues as corresponding to noise includes: selecting a first subset of the eigenvalues as corresponding to noise; calculating an average of the first subset of the eigenvalues; comparing the average of the first subset of eigenvalues to a corresponding average predicted by the general noise model; and identifying, based on the comparison, the first subset of the eigenvalues as corresponding to noise.

In still yet another variation of this embodiment, the average of the first subset of the eigenvalues is greater than the corresponding average predicted by the general noise model, and identifying the subset of the eigenvalues as corresponding to noise further includes iteratively performing, until a new average of the first subset of the eigenvalues is less than or equal to the new corresponding average predicted by the general noise model, each of: removing at least one eigenvalue from the first subset of the eigenvalues; calculating a new average of the first subset of the eigenvalues; and comparing the new average of the first subset of the eigenvalues to a new corresponding average predicted by the general noise model.

In another variation of this embodiment, a set of signal eigenvalues includes the eigenvalues without the subset of eigenvalues identified as corresponding to noise, and the method further comprises: applying a pre-calculated signal model to the set of signal eigenvalues after identifying the subset of eigenvalues as corresponding to noise.

In yet another variation of this embodiment, the machine readable instructions, when executed, further cause the system to perform, prior to identifying the one or more subsets of voxels, a noise decorrelation procedure for the scanner.

In still yet another variation of this embodiment, the noise decorrelation procedure is to decorrelate signals from one or more coils of the scanner.

In another variation of this embodiment, the machine readable instructions, when executed, further cause the system to compare the reconstructed series of MRF images to a pre-calculated dictionary; and construct, based on the comparison, at least a T1 map and a T2 map of the series of MRF images.

In yet another variation of this embodiment, the eigenvalues are complex values.

In still yet another variation of this embodiment, generating the one or more sets of eigenvectors includes performing singular vector decomposition on the one or more subsets of voxels.

In another variation of this embodiment, the singular vector decomposition is compressed singular vector decomposition.

In yet another variation of this embodiment, the patches of voxels are no larger than 3 by 3 voxel patches.

In still yet another variation of this embodiment, the system functions agnostic to the type of body tissue being scanned.

BRIEF DESCRIPTION OF THE DRAWINGS

The patent or application file contains at least one drawing executed in color. Copies of this patent or patent application publication with color drawing(s) will be provided by the United States Patent and Trademark Office upon request and payment of the necessary fee.

DETAILED DESCRIPTION

Imaging scans (such as magnetic resonance (MR) scans) performed using low-field scanners tend to output noisy data and images. As such, it can be difficult to distinguish a particular image and/or portion of an image due to the additional noise added by the scanner and/or system. Example methods, systems, and apparatuses described herein perform denoising of image data, such as magnetic resonance imaging (MRI) or magnetic resonance fingerprinting (MRF) data, using a denoising algorithm that applies a general noise model. The mathematical basis for the denoising algorithm is that eigenvalues in principal component analysis corresponding to uncorrelated Gaussian noise follow the distribution of a general noise model, such as a Marcenko-Pastur (MP) distribution. By fitting a set of eigenvalues to the general noise model, the eigenvalues of the pure noise can be determined through a comparison to the general noise model. The system may subsequently remove the noise to construct, reconstruct, and/or map denoised images. MRF systems further improve estimation due to the hundreds of undersampled time points acquired in performing an MRF function—causing noise to be redundantly measured and improving the accuracy with which denoising is performed.

After denoising image data, the system matches the image data against a pre-calculated dictionary for T1 and T2 values to retrieve T1 and T2 values for the image data. In some implementations, the pre-calculated dictionary is calculated by solving Bloch equations to simulate signal evolutions as functions of different combinations of T1 and T2 relaxation times and off-resonance frequencies. The system then constructs T1 and T2 maps using the T1 and T2 values, respectively. Normalized root mean square error (NRMSE) values of the maps compared to noiseless T1 and T2 maps display improvement compared to other such techniques, as described with regard to FIGS. 2A-2C below.

Figure 1A:
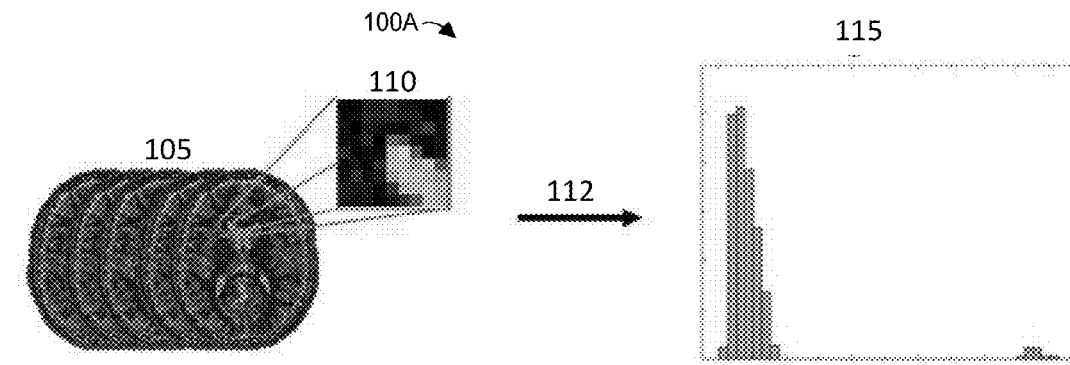
FIG. 1A illustrates a diagram depicting a method for receiving a series of images and generating a series of eigenvectors and corresponding eigenvalues.

Referring first to FIG. 1A, a diagram 100A illustrates a method for receiving a series of images and generating a series of eigenvectors and corresponding eigenvalues. The method of FIG. 1A may be implemented in an MRF system 600 as described with regard to FIG. 6 below. Though the method below is described with regard to MRF system 600, one skilled in the art will recognize that any similarly suitable system may be used to implement FIG. 1A. For example, the method of FIG. 1A may be implemented in an MRI system or another, similar imaging system.

First, a system 600 receives one or more images 105 from a fingerprinting apparatus 699 and/or some other scanning device of the system 600. In some implementations, the one or more images 105 may be a single series of images the system 600 receives simultaneously and/or in real-time. In further implementations, the one or more images 105 may be multiple series of images, and the fingerprinting apparatus 699 may transmit the one or more images 105 as each series is taken (i.e., in real-time) or the fingerprinting apparatus 699 may store each series of images and transmit the one or more images 105 as a larger group.

After receiving the one or more images 105, the system 600 separates each image into subsets or patches of voxels 110. The size of each patch may be 1×1 voxel patches, 2×2 voxel patches, 3×3 voxel patches, 4×4 voxel patches, 5×5 voxel patches, etc. In some implementations, the voxel patch size is kept small to minimize the spatial noise variation in the data. Put another way, the voxel patch size is kept small to avoid mixing signals in voxel patches. Further, smaller voxel patches creates greater redundancy between the patches. The greater redundancy allows the system 600 to generate and analyze a larger array of eigenvectors and corresponding eigenvalues, leading to greater accuracy in the denoising process.

After the system 600 separates each image into patches, the system 600 performs a denoising procedure on each patch sequentially. In the example of FIG. 1A, the system 600 performs a principal component analysis (PCA) operation. The system 600 determines the principal components prior to or as part of the PCA, the principal components including at least eigenvectors and eigenvalues for each patch of voxels. In some implementations, the PCA operation is performs a change of basis for the patches of voxels using the eigenvectors and eigenvalues for each patch of voxels. In further implementations, the PCA performs the change of basis by performing a singular value decomposition (SVD) 112 operation on each patch. The system 600 performs SVD 112 on each patch by generalizing the patch into an eigendecomposition consisting of an eigenvector and corresponding eigenvalue. In some implementations, the SVD 112 for a matrix M corresponding to the m×n voxel patch matrix can be determined according to the equation M=UΣV*, wherein U is an m×n complex unitary matrix, Σ is an m×n rectangular diagonal matrix with non-negative real numbers on the diagonal, and V is an n×n complex unitary matrix. In further implementations, the SVD is determined using SVD compression, in which the system 600 truncates the SVD and applies SVD to the pre-calculated dictionary, resulting in a compressed dictionary in the time domain, increasing the speed of the system 600 in performing the denoising procedure.

In some implementations, the system 600 generates the eigenvectors such that each eigenvector has the greatest variance possible while still being orthogonal to previous eigenvectors for previous voxel patches. Depending on the implementation, the corresponding eigenvalues for the eigenvectors correspond to the strength and/or frequency of the respective eigenvector in the dataset. In some implementations, the system 600 then plots the eigenvalues for the various eigenvectors in plot 115. In further implementations, the system 600 may generate the plot 115 of the eigenvalues for the benefit of the user and/or operator and/or in response to a command from the user and/or operator. In still further implementations, the system 600 does not generate a plot 115 at all and/or mathematically performs the functionality of the plot 115 without generating a visible plot.

Figure 1B:
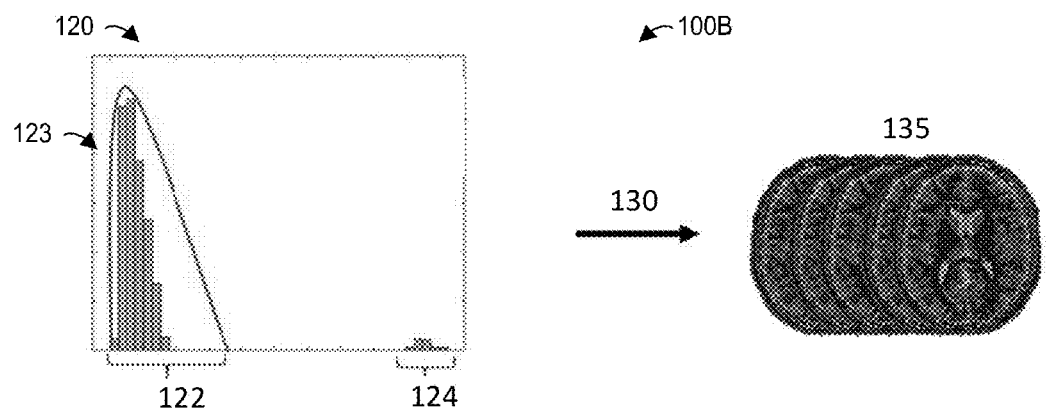
FIG. 1B illustrates a diagram depicting a method for denoising a set of eigenvalues and reconstructing a series of images, continuing from FIG. 1A.

Referring next to FIG. 1B, a diagram 100B illustrates a method for denoising a set of eigenvalues and reconstructing a series of images, continuing from FIG. 1A. Much like the method of FIG. 1A, the method of FIG. 1B may be implemented in an MRF system 600 as described with regard to FIG. 6 below. Though the method below is described with regard to system 600, one skilled in the art will recognize that any similarly suitable system may be used to implement FIG. 1B. For example, the method of FIG. 1B may be implemented in an MRI system or another, similar imaging system.

After generating and, in some implementations, plotting the eigenvalues for the patches of voxels 110, the system 600 then generates a predicted set of eigenvalues using a noise distribution model 123. The noise distribution model 123 is a general noise model, such as a Marcenko-Pastur distribution model. In implementations in which the system 600 plots the eigenvalues on a plot 115, the system 600 may create a new plot 120 using the noise distribution model 123 and the plot of eigenvalues 115. In other implementations, the system 600 may plot the eigenvalues freshly in plot 120. The system 600 compares the generated eigenvalues for the voxel patches 110 to the predicted eigenvalues of the noise distribution model 123. The system 600 uses the comparison to determine which eigenvalues correspond to noise 122 and which eigenvalues correspond to actual signals 124. In some implementations, the set of eigenvalues that correspond to noise satisfy the following equation:

$$\left(\frac{\sum_{i=1}^{p}\lambda_i}{M-p}\right) \geq \frac{\lambda_{p+1}-\lambda_M}{4\sqrt{\frac{M-p}{N}}}.$$

In further implementations, the noise eigenvalues 122 are those that fall beneath the curve of the noise distribution model 123, while the signal eigenvalues 124 are those that fall above the curve of the noise distribution model 123, as shown in FIG. 1B. Depending on the implementation, the system 600 determines which eigenvalues correspond to noise 122 and which eigenvalues correspond to signals 124 in an iterative process, as described in more detail with respect to FIG. 4 below.

Using a general noise model such as a Marcenko-Pastur distribution model provides a number of benefits over present techniques in the art. For example, because general noise models are generalized, a system 600 can analyze a greater variety and/or range data through the above methods. As such, although the above techniques are described as applied through an MRF system 600, one skilled in the art will recognize that the techniques described herein may be applied to any similar such data, such as MRI data. Present techniques, such as empirically setting thresholds or predictive thresholds, are parameter-specific and, as such, cannot be easily generalized. In part, this is due to the signal-focused nature of present techniques. The application of a general noise model rather than any signal model, for example, allows a system such as MRF system 600 to take advantage of patterns in random noise distribution such as those described by the Marcenko-Pastur distribution model in eliminating noise from a system.

After removing the noise, the system 600 performs a reverse SVD process 130 on the signal eigenvalues 124 to reconstruct denoised images 135. Though the denoised images 135 are referred to as denoised, in some implementations, a small amount of noise remains in the images, and denoising therefore refers to reducing noise is such implementations. Further, in some such implementations, the presence of a small amount of noise is due to the size of the voxel patches 110. In such implementations, the value of the average of the sum of the eigenvalues is less than the corresponding average as calculated by the general noise distribution model 123, but not equal to it, meaning that some noise is left in the images to avoid sacrificing signal eigenvalues 124. As such, the system 600 reconstructs accurate MRF images with greatly reduced noise without sacrificing speed or computation power.

Figure 1C:
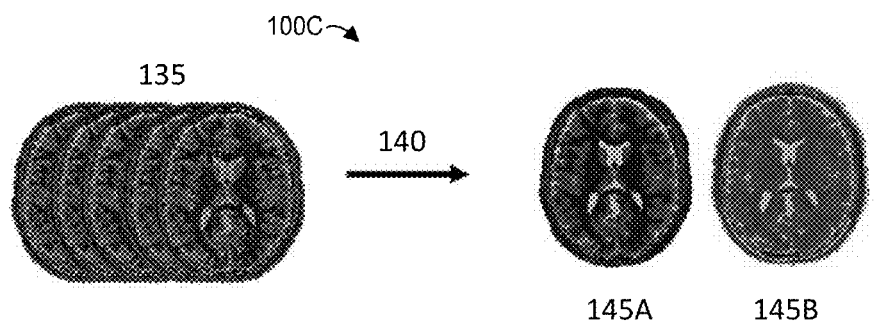
FIG. 1C illustrates a diagram depicting a method for creating a T1 map and a T2 map from the reconstructed series of images, continuing from FIG. 1B.

Referring next to FIG. 1C, a diagram 100C illustrates a method for creating a T1 map and a T2 map from the reconstructed series of images, continuing from FIG. 1B. Much like the method of FIGS. 1A and 1B, the method of FIG. 1C may be implemented in an MRF system 600 as described with regard to FIG. 6 below. Though the method below is described with regard to system 600, one skilled in the art will recognize that any similarly suitable system may be used to implement FIG. 1C. For example, the method of FIG. 1C may be implemented in an MRI system or another, similar imaging system.

After reconstructing the denoised images 135, the system 600 performs a dictionary matching procedure 140 on the denoised images 135. The system 600 uses a pre-calculated dictionary with T1 values to create a T1 map 145A and a pre-calculated dictionary with T2 values to create a T2 map 145B. In some implementations, the pre-calculated T1 dictionary has T1 values ranging from 10 milliseconds to 5000 milliseconds. In further implementations, the pre-calculated T2 dictionary has T2 values ranging from 2 milliseconds to 1200 milliseconds.

Figures 2A, 2B:
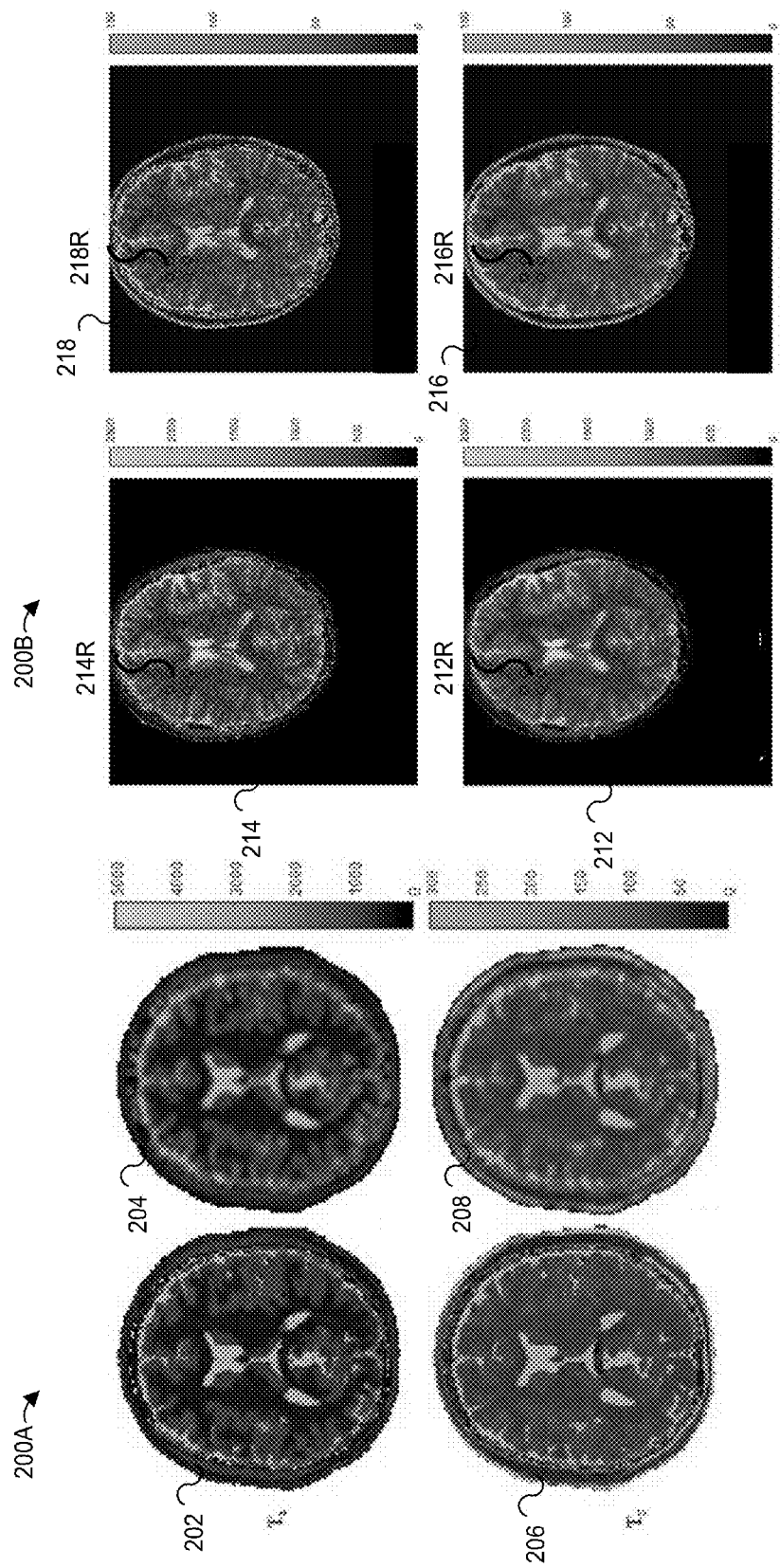
FIG. 2A illustrates a diagram depicting results for T1 and T2 maps created using the techniques described in FIGS. 1A-1C, and compares them to T1 and T2 maps created using conventional denoising techniques.
FIG. 2B illustrates a diagram depicting results for T1 and T2 maps created using the techniques described in FIGS. 1A-1C, and compares them to T1 and T2 maps created using conventional denoising techniques.

Referring next to FIGS. 2A and 2B, diagrams 200A and 200B illustrate results for T1 and T2 maps created using the techniques described above and compares them to T1 and T2 maps created using conventional denoising techniques. Though the method below is described with regard to system 600, one skilled in the art will recognize that any similarly suitable system may be used to implement the techniques of FIGS. 2A and 2B. For example, the techniques of FIGS. 2A and 2B may be implemented in an MRI system or another, similar imaging system.

Diagram 200A depicts a series of T1 and T2 maps, some generated by the proposed techniques described herein and some generated and denoised through a voxel averaging technique existing in the art. All four maps are generated using an SNR of 20. The averaged T1 map 204 and averaged T2 map 208 are generated by averaging each voxel with the 8 voxels in a 3×3 square around the voxel. Denoised T1 map 202 and denoised T2 map 206 are noticeably sharper than averaged T1 map 204 and averaged T2 map 208. The normalized root mean square error (NRMSE) with respect to a noiseless reference image is also noticeably lower for the denoised T1 map 202 and denoised T2 map 206 when compared to the averaged T1 map 204 and the averaged T2 map 208. In diagrams 200A, for example, denoised T1 map 202 has an NRMSE of 0.3050, whereas averaged T1 map 204 has an NRMSE of 0.3632. Similarly, denoised T2 map 206 has an NRMSE of 0.3449 compared to averaged T2 map 208, which has an NRMSE of 0.3833.

Diagrams 200B depict a standard T1 map 214 without denoising, a standard T2 map 218 without denoising, a denoised T1 map 212, and a denoised T2 map 216. Noticeably, the denoised maps 212 and 216 have less interference and are clearer than the T1 and T2 maps 214 and 218 without denoising. Each map also depicts a respective region of interest (ROI) 212R, 214R, 216R, and 218R. The system 600 calculates an average T1 or T2 value as appropriate within the ROIs 212R, 214R, 216R, and 218R, as well as a standard deviation. Noticeably, the standard deviation is lower in the denoised maps 212 and 216 than in the standard maps 214 and 218. For example, the average T1 value and standard deviation in the ROI 212R is 392.75±39.80 compared to the average T1 value and standard deviation in the ROI 214R, which is 403.28±118.83. Similarly the average T2 value and standard deviation in the ROI 216R is 33.74±3.77 compared to the average T2 value and standard deviation in the ROI 218R, which is 32.63±13.45.

Figure 2C:
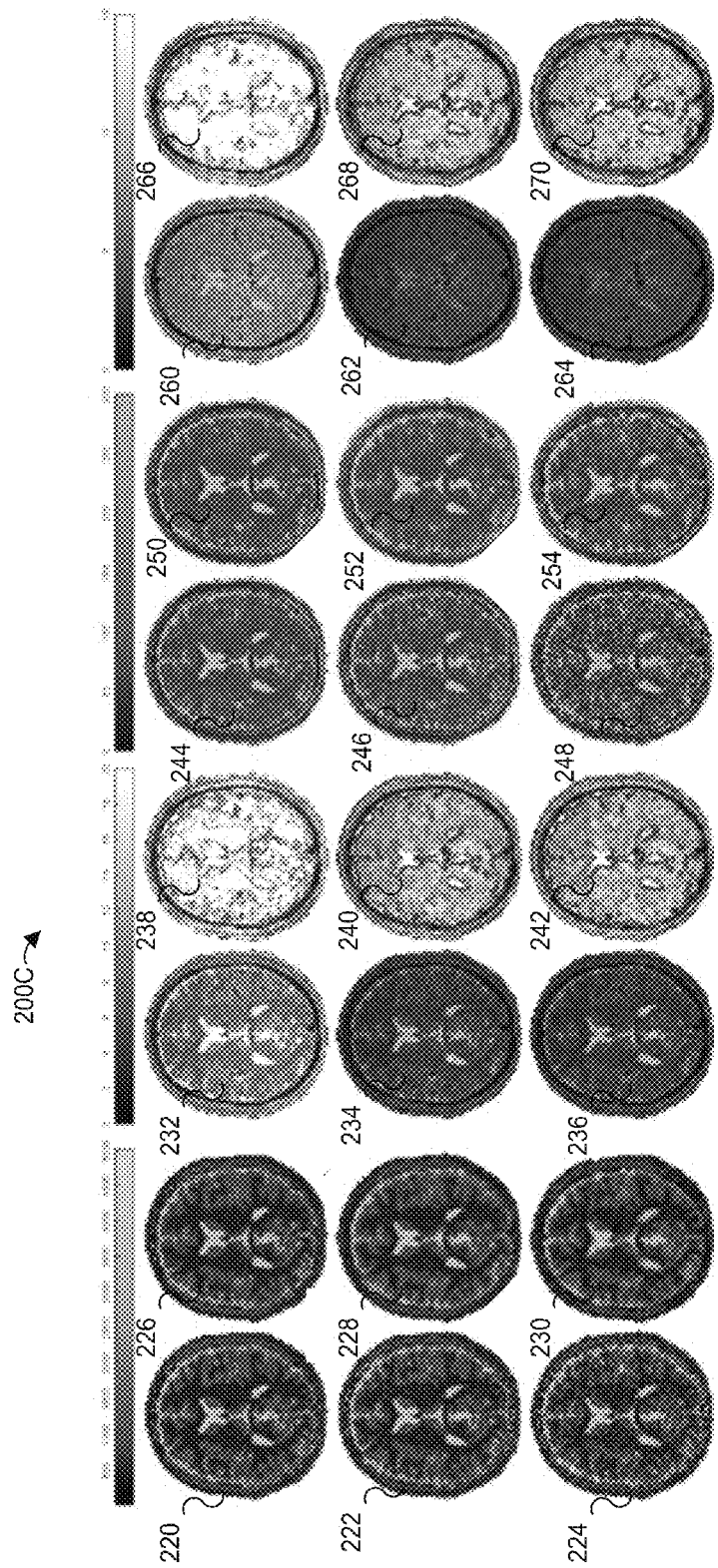
FIG. 2C illustrates a diagram depicting results for T1 and T2 maps for noisy and denoised maps as well as SNR maps.

Referring next to FIG. 2C, diagrams 200C illustrate results for T1 and T2 maps for noisy and denoised maps as well as SNR maps. Maps 220, 222, 224, 226, 228, and 230 (T1 maps 220-230) are T1 maps; maps 244, 246, 248, 250, 252, and 254 (T2 maps 244-254) are T2 maps; and maps 232, 234, 236, 238, 240, 242 (T1 SNR maps 232-242) and maps 260, 262, 264, 266, 268, and 270 (T2 SNR maps 260-270) are SNR maps of T1 and T2, respectively. T1 SNR maps 232-242 and T2 SNR maps 260-270 are estimated using multiple replicas using a bootstrapped Monte Carlo method.

T1 maps 220, 222, and 224; T1 SNR maps 232, 234, 236; T2 maps 244, 246, and 248; and T2 SNR maps 260, 262, and 264 are maps constructed using noisy data. T1 maps 226, 228, and 230; T1 SNR maps 238, 240, and 242; T2 maps 250, 252, and 254; and T2 SNR maps 266, 268, and 270 are maps constructed using denoised data via methods described herein. Each of T1 maps 220 and 226 as well as T2 maps 244 and 250 are constructed using an SNR of 20. Similarly, maps 222, 228, 246, and 252 are constructed using an SNR of 10 and maps 224, 230, 248, and 254 are constructed using an SNR of 5. T1 SNR maps 232-242 and T2 SNR maps 260-270 are constructed to measure the performance of denoising. The T1 SNR maps 232-242 and T2 SNR maps 260-270 are the standard deviation of T1 or T2, respectively, divided by the mean T1 or T2 value. In some embodiments, each of the T1 maps 220-230 and T2 maps 244-254 have a corresponding normalized root mean square error (NRMSE) calculated using a corresponding noiseless image.

In such implementations, each of the denoised T1 maps 226, 228, and 230 has a comparable or better NRMSE than the corresponding noisy T1 maps 220, 224, and 226. Similarly, each denoised T2 map 250, 252, and 254 has a lower (and thus improved) or comparable NRMSE compared to each corresponding noisy T2 map 244, 246, and 248. Further, each denoised SNR map 238, 240, 242, 266, 268, and 270 has improved SNR throughout compared to the noisy SNR maps 232, 234, 236, 260, 262, and 264. As such, one skilled in the art will recognize the improvements offered using the denoising methods described herein when compared to standard noise or using denoising techniques currently known in the art.

Figure 3:
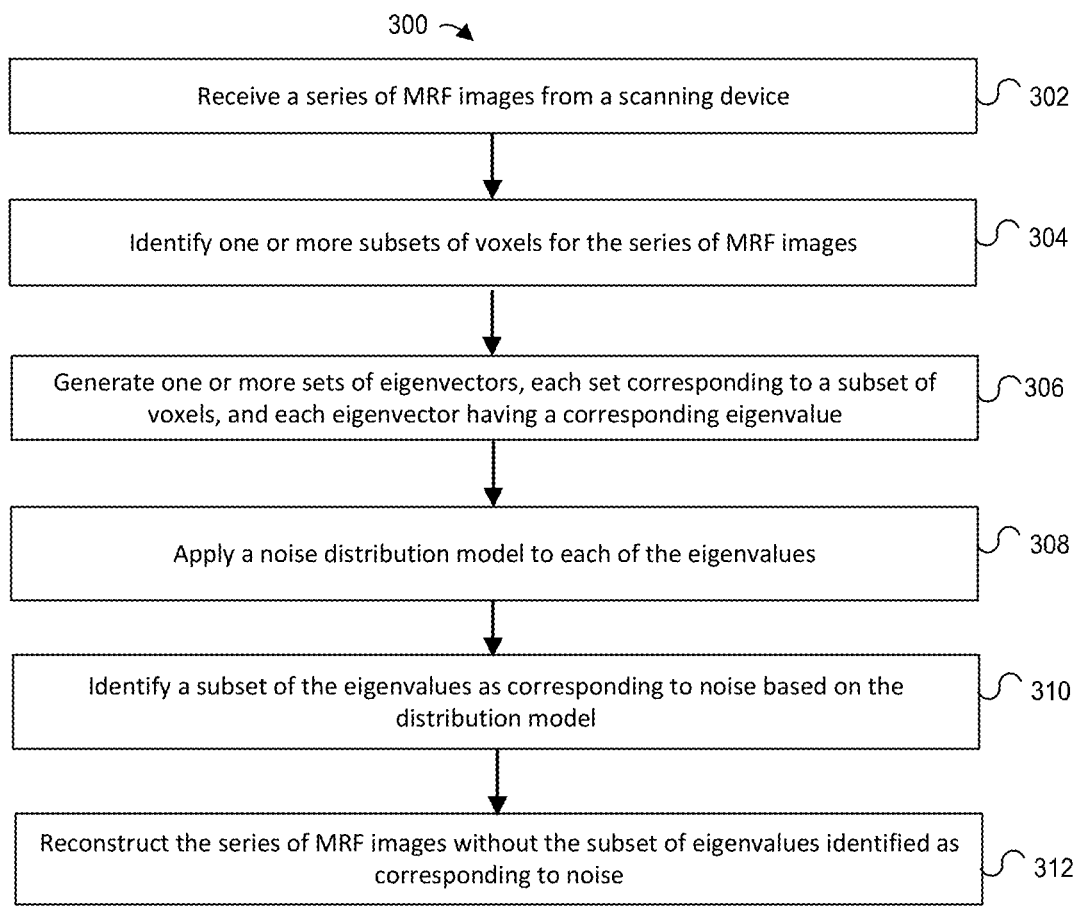
FIG. 3 illustrates an example flowchart depicts a method for denoising MRF acquisitions.

Referring next to FIG. 3, a flowchart 300 illustrates a method for denoising MRF acquisitions. For the sake of clarity, FIG. 3 is discussed with regard to an MRF system 600, a computing device 670, and a fingerprinting apparatus 699, all illustrated in FIG. 6 and described below. However, any similarly suitable scanning device, computing device, or system may be used to implement the techniques of flowchart 300.

At block 302, one or more processors of a computing device 670 of an MRF system 600 receive a series of images from a fingerprinting apparatus 699 or a similar scanning device. In a preferred embodiment, the one or more processors receive a series of MRF images. Although the flowchart 300 describes a preferred embodiment, depending on the implementation, the processors may receive any similar image data. For example, the scanning device 699 may transmit MRF image data, MRI image data, or any other similar image data.

At block 304, the MRF system 600 identifies one or more subsets of voxels for the series of images and/or image data received. In a preferred embodiment, the subsets of voxels may be 1×1 voxel patches, 2×2 voxel patches, 3×3 voxel patches, 4×4 voxel patches, 5×5 voxel patches, or any other similarly sized voxel patches. In some implementations, the voxel patches are small enough to only cover redundant data so as to avoid unnecessary correlation in signals and/or misclassifying signal as noise or vice versa.

In some implementations, the MRF system 600 performs a noise decorrelation procedure prior to identifying the subsets of voxels. The system 600 performs the noise decorrelation procedure on MRF data extracted from the MRF images and decorrelates signals from one or more coils of the scanner and/or the MRF system 600. The coils of the MRF system 600 may naturally cause correlation between the various signals gleaned and analyzed by other elements of the MRF system 600. As such, performing a noise decorrelation procedure ensures that the signals are not correlated, preventing and/or reducing the possibility of the coils skewing the output when MRF system 600 applies a noise distribution as described below with regard to block 308. Depending on the implementation, the noise decorrelation procedure may be a pre-whitening procedure, a randomness extraction procedure, or any other similar noise decorrelation procedure known in the art.

At block 306, the MRF system 600 generates one or more sets of eigenvectors based on the subsets of voxels. In some implementations, the MRF system 600 generates the eigenvectors using singular vector decomposition (SVD). Depending on the implementation, the SVD may be compressed SVD or uncompressed SVD. In compressed SVD, a reduced number of voxels are analyzed, whereas the entire range is analyzed using uncompressed SVD. For example, compressed SVD may analyze 15 data points compared to uncompressed SVD, which may analyze 3000 data points.

At block 308, the MRF system 600 applies a noise distribution model to each of the eigenvalues corresponding to the eigenvectors. The noise distribution model is a general noise model such as a Marcenko-Pastur distribution model. In some implementations, the MRF system 600 applies the noise distribution model by matching the measured eigenvalues with an expected random distribution of noise as described by the general noise model. For example, the MRF system 600 may plot eigenvalues and an average value according to a Marcenko-Pastur distribution as illustrated in plot 120 of FIG. 1B. By applying the noise distribution model to each eigenvalue, the system 600 determines which measured eigenvalues—and, as such, which patches of voxels in the image(s)—correspond with noise. In some implementations, the system 600 classifies any eigenvalues that match the noise distribution model as noise. In further implementations, the system 600 classifies any eigenvalues that fall below the noise distribution model or an average of the noise distribution model as noise. In still further implementations, should the system 600 classify all eigenvalues as noise, the greatest value eigenvalue will be automatically reclassified as a signal to prevent excessive denoising.

In some implementations, the system 600 matches the eigenvalues and/or image data to multiple physical models rather than a single noise distribution model. In some such implementations, one of the physical models is the single noise distribution model while another physical model is a pre-calculated signal model for generating quantitative information about the received image data. For example, the pre-calculated signal model may provide information about one or more traits of the tissue(s) being scanned and/or information relevant and/or visible in the mapped T1 and T2 images. In such implementations, the system 600 applies the pre-calculated signal model to the image data after the system 600 applies the noise distribution model to remove noise.

In further implementations, the eigenvalues are sorted based on how much each eigenvalue contributes to the overall variance of the data. As the data is assumed to be (or the system 600 performs a process to ensure, depending on the implementation and as described above) decorrelated, the system 600 determines that correlations that are identified in the data (and, as such, cause a greater impact on the overall variance) are "signal" data. The repetition in output signals suggests that such signals are intentional—i.e. are not noise. In some implementations, the system 600 learns and/or trains an algorithm/model based on the repetition. Depending on the implementation, the system 600 may train the algorithm and/or model using machine learning techniques.

As such, data that has minimal and/or less contribution than other data is deemed to be more likely to be noise. In some implementations, such repetition is borne from redundant images. In such implementations, MRF imaging improves the functionality of the system 600. One skilled in the art will recognize that MRF imaging techniques naturally produce large quantities of such redundant images. As such, an MRF imaging system 600 may increase the overall accuracy and performance of such a denoising algorithm with minimal or no costs. However, depending on the implementation, the denoising algorithms may function with less repetition at the cost of accuracy and/or performance.

At block 310, the MRF system 600 then identifies a set of the eigenvalues as corresponding to noise based on the distribution model. For example, the MRF system 600 may determine that the set of eigenvalues falling under the curve described by the Marcenko-Pastur distribution corresponds to noise in the system. Subsequently, at block 312, the MRF system 600 reconstructs the series of MRF images without the set of eigenvalues identified as corresponding to noise.

One skilled in the art will recognize that, while performing method 300 on a series of images taken by an MR Fingerprinting apparatus and/or scanner, the MRF system 600 uses the complex values of the eigenvalues rather than the absolute value for more accurate results. As such, in such implementations the eigenvalues are complex values. In alternative implementations, such as in implementations in which an MRI system performs method 300 on a series of images taken by an MRI apparatus and/or scanner, the system may instead use absolute value for the eigenvalues rather than a complex value.

In some implementations, after reconstructing the series of MRF images without the noise, the MRF system 600 constructs a T1 map and a T2 map for the series of MRF images. The MRF system 600 may construct the T1 map and T2 map by comparing the reconstructed series of MRF images and/or reconstructed MRF image data to a pre-calculated dictionary. In some such implementations, the MRF system 600 uses a pattern recognition algorithm to match the reconstructed MRF image data to an entry from a dictionary of possible signal evolutions created by simulation of the sequence and a range of biologically relevant relaxation parameters (i.e., the T1 and T2 parameter values).

Put another way, the MRF system 600 compares the reconstructed data to a dictionary correlating T1 and T2 values with expected possible signal evolutions to determine T1 and/or T2 values for each voxel of a reconstructed MRF image. In some implementations, the MRF system 600 uses extended phase graph (EPG) techniques to construct the T1 and/or T2 dictionaries. In other implementations, the MRF system 600 constructs the T1 map and T2 map by using other techniques known in the art, such as Bloch simulation.

In further implementations, the MRF system 600 applies a second model after identifying the subset of eigenvalues as corresponding to noise. The second model, depending on the implementation, may be a pre-calculated signal model that produces quantitative information with regard to MRF data and the MRF images. For example, the second model may produce information related to the (k, t, E) space of the MRF images as described below with regard to FIG. 6. In such implementations, the MRF system 600 applies the second model in place of or in addition to reconstructing the series of MRF images. Further, the MRF system 600 may apply the second model after matching the signal from the MRF system 600 to the general noise model to remove the noise, as described above.

Figure 4:
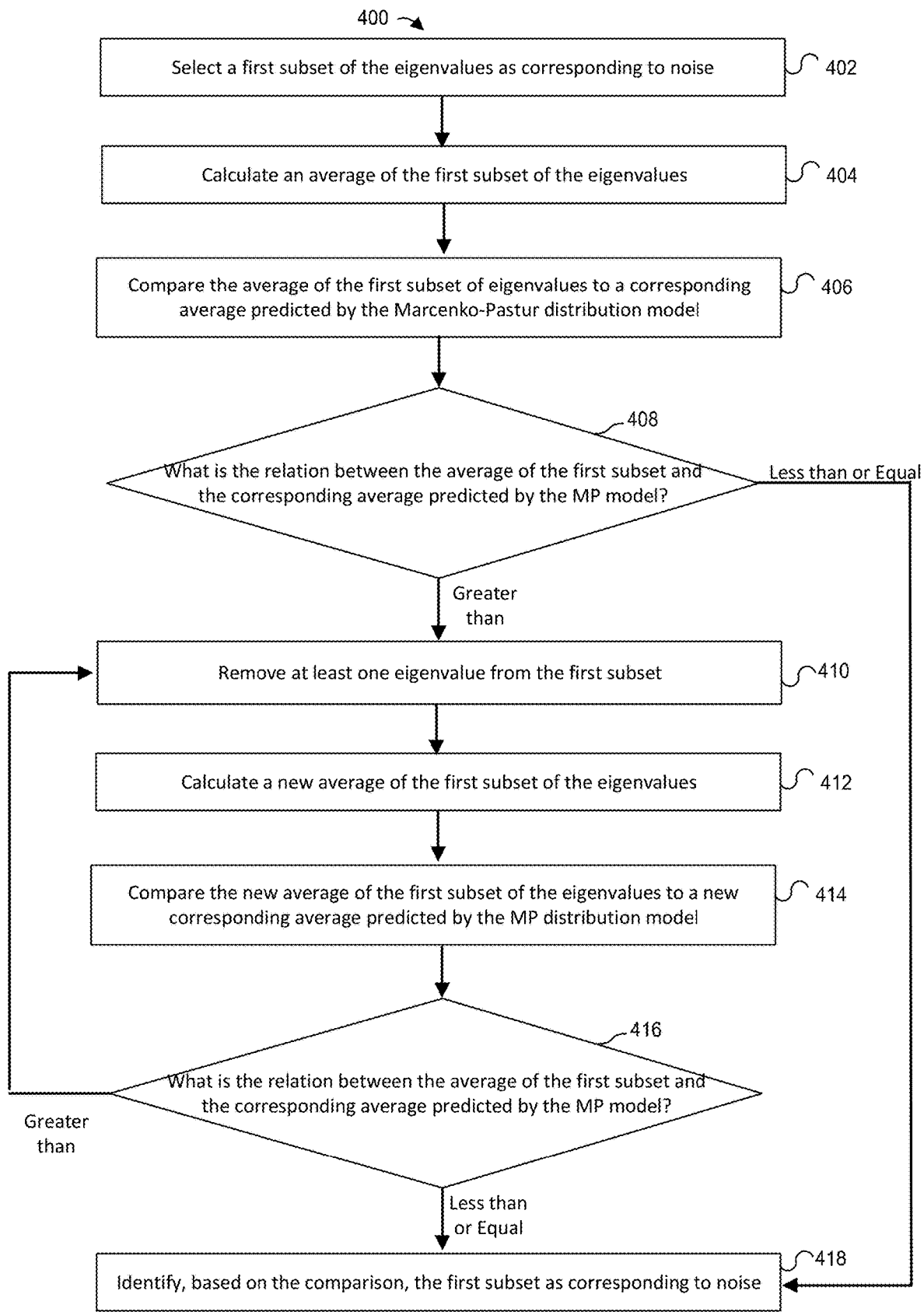
FIG. 4 illustrates an example flowchart depicts a method for denoising MRF acquisitions, to be implemented as part of the method of FIG. 3.

Referring next to FIG. 4, a flowchart 400 illustrates a method for denoising MRF acquisitions. For the sake of clarity, FIG. 4 is discussed with regard to the MRF system 600 as described with regard to FIG. 6 below. However, any similarly suitable imaging system may be used to implement the techniques of flowchart 400.

In some implementations, flowchart 400 takes place as part of or immediately before block 310 of flowchart 300 and/or as part of a PCA procedure. In other implementations, flowchart 400 takes place as part of a similar method as that described by flowchart 300. In yet other implementations, flowchart 400 is independent of any such method as described by flowchart 300. At block 402, the MRF system 600 begins to determine the principal components for the PCA by first selecting a first subset of the eigenvalues as corresponding to noise. In some implementations, the MRF system 600 selects the subset of the eigenvalues according to commands and/or input from a user. In other implementations, the MRF system 600 automatically selects a subset of eigenvalues based on a predetermined method and/or based on traits of the MRF images. For example, the MRF system 600 may automatically select all eigenvalues or all eigenvalues except the greatest value eigenvalue as corresponding to noise. Alternatively, the MRF system 600 may select only the lowest value eigenvalue as corresponding to noise. In still other implementations, the MRF system 600 selects the initial eigenvalues based on a previously analyzed MRF image in the series. For example, the MRF system 600 may determine that a previously analyzed MRF image is similar to an MRF image that the MRF system 600 is analyzing. As such, the MRF system 600 may determine to initially select a first n eigenvalues as noise, where n is the number of eigenvalues that corresponded to noise in the previous MRF image.

At block 404, a computing device of the MRF system 600 calculates an average of the first subset of the eigenvalues and, at block 406, the MRF system 600 compares the average of the first subset of eigenvalues to a corresponding average predicted by the general noise model. In some implementations, the MRF system 600 compares the averages by additionally or alternatively identifying the significant signal components by satisfying the equation $$\left(\frac{\sum_{i=1}^{p} \lambda_i}{M-p}\right) \geq \frac{\lambda_{p+1} - \lambda_M}{4\sqrt{\frac{M-p}{N}}},$$

wherein the SVD is of size M×N and the p is the size of the set of significant signal eigenvalues. For example, a computing device of the system 600 may remove eigenvalues from the set of selected noisy eigenvalues, thereby increasing p by one. When the equation is satisfied (i.e., the average of the first subset of eigenvalues is less than or equal to the corresponding average predicted by the general noise model), the system 600 determines that the set of noise values is complete, as described in more detail with regard to block 408 below.

At decision block 408, the system 600 determines what the relation between the average of the first subset and the corresponding average predicted by the general noise model is. If the average of the first subset is less than or equal to the corresponding average predicted by the general noise model, then the system 600 has determined the set of principal components and flow continues directly to block 418. Otherwise, if the average of the first subset is greater than the corresponding average predicted by the general noise model, then the flow continues directly to block 410 and begins modifying the set of principal components. When the average of the first subset is greater than the corresponding average predicted by the general noise model, the MRF system 600 determines that the set of eigenvalues corresponding to noise is too large, and—as such—includes some number of eigenvalues that correspond to signals. As such, at block 410, the MRF system 600 removes at least one eigenvalue from the first subset. In some implementations, the MRF system 600 automatically removes one eigenvalue in response to the determination at block 408. In further implementations, the MRF system 600 may prompt a user to remove and/or approve removal of eigenvalue(s) from the set. In still further implementations, the MRF system may determine to remove multiple eigenvalues from the set, based on the amount by which the average of the first subset exceeds the corresponding predicted average.

At block 412, the MRF system 600 calculates a new average of the subset of the eigenvalues using the new, reduced subset of eigenvalues. Subsequently, at block 414, the MRF system 600 compares the new average of the subset of the eigenvalues to a new corresponding average predicted by the general noise distribution model.

At block 416, the MRF system 600 reaches another decision block similar to block 408 and determines what the relation is between the new average of the first subset and the new corresponding average predicted by the general noise distribution model. Much like block 408, if the MRF system 600 determines that the new average is less than or equal to the new corresponding average, flow continues to block 418. Otherwise, if the MRF system 600 determines that the new average is greater than the new corresponding average, the flow loops back to block 410 to repeat blocks 410-416. As such, the system 600 iteratively removes eigenvalues from the set of noisy eigenvalues until the system 600 determines a set of eigenvalues designated as noise. At block 418, the system 600 determines that the first subset corresponds to noise based on the results of the comparison and the system 600 compares the principal components to the general noise model. For example, the system 600 determines that the first subset includes all of the eigenvalues that fall below the curve of a Marcenko-Pastur distribution of noise, and thus includes all or most of the noise.

Though FIG. 4 illustrates a particular embodiment of a method for identifying noise, one skilled in the art will recognize that the instant method covers further potential embodiments. For example, in some implementations, the MRF system 600 removes multiple eigenvalues from the set of values at block 410. In such implementations, the MRF system 600 then, after determining that the new average is less than the new corresponding average, adds some of the removed eigenvalues back into the set of values, calculates a new average, and compares the new average to the new corresponding average. In such implementations, the MRF system 600 repeats the addition process until the new average is greater than the new corresponding average, at which point the MRF system 600 may revert back to the removal process described in blocks 410-416. The MRF system 600 may repeat both cycles, progressively decreasing the number of eigenvalues added and/or removed with each iteration. As such, the MRF system 600 may "bounce" the set of eigenvalues between containing too many eigenvalues and too few eigenvalues until finding a homeostasis point.

Figure 5:
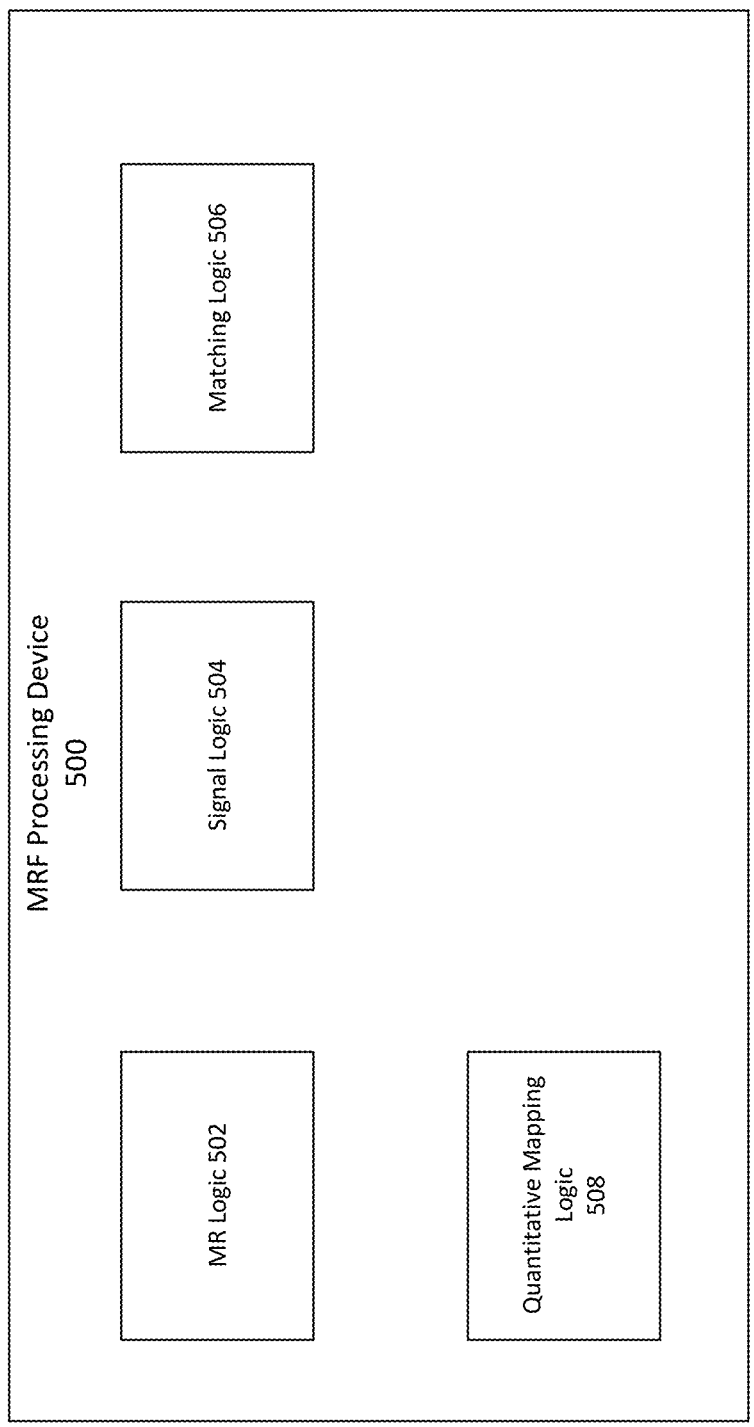
FIG. 5 illustrates an example MRF processing device in which the techniques of FIGS. 1A-4 may be implemented.

Referring next to FIG. 5, MRF processing device 500 is a processing device for analyzing MR images, and includes one or more logic modules 502, 504, 506, and/or 508. Depending on the implementation, the logic modules 502, 504, 506, and/or 508 may be implemented in the MRF processing device 500 as hardware, software, firmware, or some combination of such. MRF processing device 500 simultaneously quantifies MR parameters including T1, T2, proton density, and the apparent diffusion coefficient (ADC) for an object to which the MRF processing device 500 applies an MRF pulse sequence. In one embodiment, MRF processing device 500 provides an MR image that facilitates identifying certain tissues based on their relative hypointense or hyper-intense appearance on an MR image (e.g., T1 weighted image, T2 weighted image).

MRF processing device 500 includes an MR logic module 502. The MR logic module 502 repetitively and variably samples an object in a (k, t, E) space to acquire a set of MR signals that may have non-constant amplitude and/or phase. For the (k, t, E) space, the k may be a point in k-space representing a spatial frequency of an MR image. In some implementations, the MR logic 502 may determine the value of k based on a Fourier Transform (FT) of the MR image. The tin the (k, t, E) space represents time, and the E represents one or more MR parameters for the MR image in question. Members of the set of MR signals are associated with different points in the (k, t, E) space. In different embodiments, the different points are sampled according to a plan where t and/or E varies non-linearly and/or in a non-constant manner.

The MR logic module 502 may sample the object using a diffusion-weighted double-echo pulse sequence. In some embodiments, the MR logic module 502 may employ a spiral readout. The pulse sequence may produce multiple signals per cycle of repetition time (TR). For example, both a free induction decay (FID) signal and an echo signal may be produced per TR. In some implementations, the FID signal is acquired using a variable density spiral-out trajectory and the spin echo signal is acquired using a variable density spiral-in trajectory. In further implementations, one signal may be more attuned with either of the T1 image or the T2 image. For example, the FID signal may be more T1-weighted and the echo signal may be more T2-weighted.

In still further implementations, the MR logic module 502 may insert a mono-polar diffusion gradient between the FID and the spin echo. Inserting the mono-polar diffusion gradient may increase the diffusion sensitivity of the pulse sequence. In some embodiments, the MR logic module 502 may acquire the FID and the spin echo with varying flip angles, varying repetition times, and varying diffusion gradient moments.

In some embodiments, MRF processing device 500 also includes a signal logic module 504. Signal logic module 504 produces an MR signal evolution from the acquired MR signals. The signal evolution may include a number of MR signals acquired over a period of time. The set of MR signals may include transient-state signals associated with the MRF pulse sequence, a free induction decay signal, and a spin echo signal.

In further embodiments, MRF processing device 500 also includes a comparison logic module 506. The comparison logic module 506 compares reference information with at least one of the produced MR signal evolution or information associated with the produced MR signal evolution. In some implementations, the comparison logic module 506 determines whether a match exists between signals included in the reference information and at least one of the produced MR signal evolution or information associated with the produced MR signal evolution based on whether the comparison logic module 506 determines there to be an exact match. In other implementations, an exact match is not necessary, and the comparison logic module 506 may determine that there exists a match where signals are similar. Depending on the implementation, a match may be the signal that most closely matches another signal and/or the first signal that matches another signal to within a threshold. A match may be found by template matching, pattern matching, or other comparison approaches. The reference information may be, for example, a previously acquired signal evolution, a simulated signal evolution, an item derived from a signal evolution other than the produced MR signal evolution, and/or any other similar information. The reference information may include signal evolutions from different tissue types (e.g., healthy, diseased, advanced disease, etc.).

In still further embodiments, MRF processing device 500 also includes a quantitative mapping logic module 508. Quantitative mapping logic module 508 simultaneously produces quantitative maps for T1, T2, proton density, and diffusion associated with the object being scanned, based at least in part on the stored signal evolution that matches the MR signal evolution. The MR parameters may be retrieved from a data store that links stored MR parameters to the reference information. Quantitative mapping logic module 508 may also display the quantitative maps or cause the quantitative maps to be displayed.

While comparison logic module 506 and quantitative logic module 508 are illustrated as being part of MRF processing device 500, in some embodiments, the comparison logic module 506 and quantitative mapping logic module 508 may reside in an apparatus separate from the MRF processing device 500. In such embodiments, MRF processing device 500 may provide MR signals to the separate apparatus housing comparison logic module 506 or quantitative mapping logic module 508. In further embodiments, comparison logic module 506 and/or quantitative mapping logic module 508 may reside in separate apparatuses.

Figure 6:
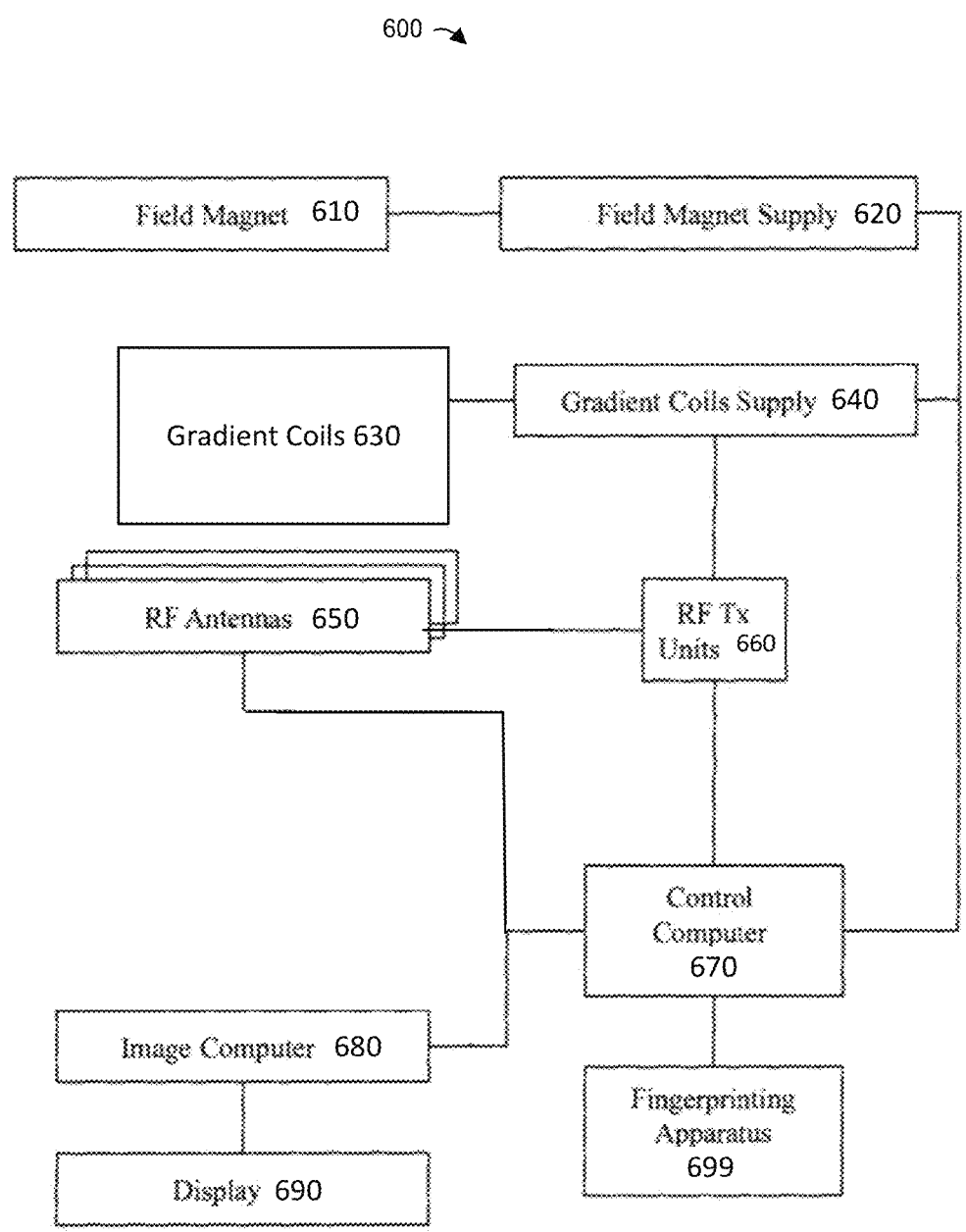
FIG. 6 illustrates an example MRF system which may include the MRF processing device of FIG. 5 and in which the techniques of FIGS. 1A-4 may be implemented.

Referring next to FIG. 6, MRF system 600 is an example MR system configured with a fingerprinting apparatus 699 to facilitate MR fingerprinting. Depending on the implementation, the fingerprinting apparatus 699 is and/or includes elements of MRF processing device 500 as described with regard to FIG. 5 above. In further implementations, the fingerprinting apparatus 699 performs example methods such as example methods 300 and/or 400 as described above. While fingerprinting apparatus 699 is illustrated as part of MRF system 600 in one example, fingerprinting apparatus 699 may be a separate apparatus or apparatuses.

The system 600 includes one or more field magnets 610 and a field magnet supply 620. In some implementations, the field magnets 610 produce a uniform $B_0$ field—i.e. the main static magnetic field of the MRF system 600. However, in other implementations, the $B_0$ field is not uniform. In such implementations, the magnetic field instead varies over an object that the MRF system 600 analyzes. MRF system 600 further includes gradient coils 630 configured to emit gradient magnetic fields. The gradient coils 630 may be controlled, at least in part, by a gradient coil supply 640. In some implementations, the timing, strength, and orientation of the gradient magnetic fields may be controlled, and thus selectively adapted, during an MR procedure. As described above, the gradient coils 630 may commonly correlate signals with each other. As such, in some implementations, the system 600 may mistake noise from multiple coils as being an actual signal, resulting in skewed denoising. In such implementations, to counter such correlation, the system 600 performs a decorrelation procedure before performing the techniques described in FIGS. 1A-4. The decorrelation procedure may be a pre-whitening procedure, an extraction procedure, or any other similar procedure as known in the art.

In some implementations, MRF system 600 includes a set of RF antennas 650 that generate RF pulses and receive resulting MR signals from an object that the MRF system 600 scans—i.e. the object to which the RF antennas 650 direct the RF pulses. In further implementations, the MRF system 600 controls how the pulses are generated and how the resulting MR signals are received. As such, the MRF system 600 may selectively adapt both operations during an MR procedure. In some implementations, the RF antennas 650 employs separate RF transmission and reception coils. Similarly, the RF antennas 650 may be controlled at least in part by a set of RF transmission units 660.

In some implementations, a control computer 670 controls some or all of the field magnet supply 620, the gradient coils supply 640, and/or the RF transmission units 660. In further implementations, the control computer 670 is further programmed to control an MR device such as MRF processing device 500. In other implementations, control computer 670 is or includes elements of MRF processing device 500. Conventionally, the MRF system 600 employs the MR signals received from the RF antennas 650 to generate an MRF image, and thus may be subject to a transformation process. In some implementations, the transformation process is or is akin to a two dimensional fast Fourier transform (FFT) that generates pixilated image data. Depending on the implementation an image computer 680 may perform the transformation. In other implementations, another, similar processing device performs the image transformation. Depending on the implementation, the display 690 may then display the image data. In some implementations, the display 690 may display some or all of the plots described with regard to FIGS. 1A-1C above. For example, the display 690 may display the plot of eigenvalues 115 and the combined plot 120 plotting the noise eigenvalues 122, the signal eigenvalues 124, and the general noise model 123.

Fingerprinting apparatus 699 facilitates the unconventional techniques for MR image reconstruction and denoising as described herein. Further, the fingerprinting apparatus 699 facilitates the construction of images from MR signals received from the RF antennas 650. As such, the RF energy applied to an object by system 600 need not be constrained to produce signals with substantially constant amplitudes or phases. Instead, fingerprinting apparatus 699 facilitates matching received signals to known signals for which a reconstruction parameter, relaxation parameter, or other information is already available.

While FIG. 6 illustrates an example MRF system 600 that includes various components connected in various ways, one skilled in the art will appreciate that other MR systems may include other components connected in other ways.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings. Additionally, the described embodiments/examples/implementations should not be interpreted as mutually exclusive, and should instead be understood as potentially combinable if such combinations are permissive in any way. In other words, any feature disclosed in any of the aforementioned embodiments/examples/implementations may be included in any of the other aforementioned embodiments/examples/implementations.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover, in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

Moreover, the patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

What is claimed is:

1. A method for denoising magnetic resonance fingerprinting (MRF) acquisitions, the method comprising:
   receiving, by one or more processors, a series of MRF images from a scanning device;
   performing, by the one or more processors, a noise decorrelation procedure for the scanning device;
   identifying, by the one or more processors and after the noise decorrelation procedure, one or more subsets of voxels for the series of MRF images;
   generating, by the one or more processors, one or more sets of eigenvectors, each set of the one or more sets of eigenvectors corresponding to one of the one or more subsets of voxels, and each eigenvector of the one or more sets of eigenvectors having a corresponding eigenvalue;
   applying, by the one or more processors, a noise distribution model to each of the eigenvalues;
   identifying, by the one or more processors, a subset of the eigenvalues as corresponding to noise based on the noise distribution model; and
   reconstructing, by the one or more processors, the series of MRF images without the subset of eigenvalues identified as corresponding to noise.

2. The method of claim 1, wherein the noise distribution model is a general noise model.

3. The method of claim 2, wherein the general noise model follows a Marcenko-Pastur distribution.

4. The method of claim 2, wherein identifying the subset of the eigenvalues as corresponding to noise includes:
   selecting a first subset of the eigenvalues as corresponding to noise;
   calculating an average of the first subset of the eigenvalues;
   comparing the average of the first subset of eigenvalues to a corresponding average predicted by the general noise model; and
   identifying, based on the comparison, the first subset of the eigenvalues as corresponding to noise.

5. The method of claim 4, wherein the average of the first subset of the eigenvalues is greater than the corresponding average predicted by the general noise model, and wherein identifying the subset of the eigenvalues as corresponding to noise further includes iteratively performing, until a new average of the first subset of the eigenvalues is less than or equal to the new corresponding average predicted by the general noise model, each of:
   removing at least one eigenvalue from the first subset of the eigenvalues;
   calculating a new average of the first subset of the eigenvalues; and
   comparing the new average of the first subset of the eigenvalues to a new corresponding average predicted by the general noise model.

6. The method of claim 2, wherein a set of signal eigenvalues includes the eigenvalues without the subset of eigenvalues identified as corresponding to noise, the method further comprising:
   applying a pre-calculated signal model to the set of signal eigenvalues after identifying the subset of eigenvalues as corresponding to noise.

7. The method of claim 1, wherein the noise decorrelation procedure is to decorrelate signals from one or more coils of the scanning device.

8. The method of claim 1, further comprising:
   comparing the reconstructed series of MRF images to a pre-calculated dictionary; and
   constructing, based on the comparison, at least a T1 map and a T2 map of the series of MRF images.

9. The method of claim 1, wherein the eigenvalues are complex values.

10. The method of claim 1, wherein generating the one or more sets of eigenvectors includes performing singular vector decomposition on the one or more subsets of voxels.

11. The method of claim 10, wherein the singular vector decomposition is compressed singular vector decomposition.

12. The method of claim 1, wherein the subsets of voxels are no larger than 3 by 3 voxel patches.

13. The method of claim 1, wherein the method is performed agnostic to the type of body tissue being scanned.

14. A system for denoising magnetic resonance fingerprinting (MRF) acquisitions, the system comprising:
   a scanning device configured to perform MRF operations and transmit a series of MRF images; and
   one or more processors and computer-readable media storing machine readable instructions that, when executed, cause the system to:
      receive the series of MRF images from the scanning device;
      perform a noise decorrelation procedure for the scanning device;
      identify, after the noise decorrelation procedure, one or more subsets of voxels for the series of MRF images;
      generate one or more sets of eigenvectors, each set of the one or more sets of eigenvectors corresponding to one of the one or more subsets of voxels and each eigenvector of the one or more sets of eigenvectors having a corresponding eigenvalue;
      apply a noise distribution model to each of the eigenvalues;
      identify a subset of the eigenvalues as corresponding to noise based on the noise distribution model; and
      reconstruct the series of MRF images without the subset of eigenvalues identified as corresponding to noise.

15. The system of claim 14, wherein the noise distribution model is a general noise model.

16. The system of claim 15, wherein the general noise model follows a Marcenko-Pastur distribution.

17. The system of claim 15, wherein identifying the subset of the eigenvalues as corresponding to noise includes:
   selecting a first subset of the eigenvalues as corresponding to noise;
   calculating an average of the first subset of the eigenvalue;
   comparing the average of the first subset of eigenvalues to a corresponding average predicted by the general noise model; and
   identifying, based on the comparison, the first subset of the eigenvalues as corresponding to noise.

18. The system of claim 17, wherein the average of the first subset of the eigenvalues is greater than the corresponding average predicted by the general noise model, and wherein identifying the subset of the eigenvalues as corresponding to noise further includes iteratively performing, until a new average of the first subset of the eigenvalues is less than or equal to the new corresponding average predicted by the general noise model, each of:
   removing at least one eigenvalue from the first subset of the eigenvalues;
   calculating a new average of the first subset of the eigenvalues; and
   comparing the new average of the first subset of the eigenvalues to a new corresponding average predicted by the general noise model.

19. The system of claim 15, wherein a set of signal eigenvalues includes the eigenvalues without the subset of eigenvalues identified as corresponding to noise, and wherein the one or more processors and computer-readable media stores further machine readable instructions that, when executed, cause the system to:
   apply a pre-calculated signal model to the set of signal eigenvalues after identifying the subset of eigenvalues as corresponding to noise.

20. The system of claim 14, wherein the noise decorrelation procedure decorrelates signals from one or more coils of the scanning device.

21. The system of claim 14, wherein the one or more processors and computer-readable media stores further machine readable instructions that, when executed, cause the system to:
   compare the reconstructed series of MRF images to a pre-calculated dictionary;
   construct, based on the comparison, at least a T1 map and a T2 map of the series of MRF images.

22. The system of claim 14, wherein the eigenvalues are complex values.

23. The system of claim 14, wherein generating the one or more sets of eigenvectors includes performing singular vector decomposition on the one or more subsets of voxels.

24. The system of claim 23, wherein the singular vector decomposition is compressed singular vector decomposition.

25. The system of claim 14, wherein the subsets of voxels are no larger than 3 by 3 voxel patches.

26. The system of claim 14, wherein the system functions agnostic to the type of body tissue being scanned.

* * * * *